US006220257B1

(12) United States Patent
Meyer et al.

(10) Patent No.: US 6,220,257 B1
(45) Date of Patent: *Apr. 24, 2001

(54) APPARATUS AND METHOD FOR POSITIONING AND MOVING A FLEXIBLE ELEMENT

(75) Inventors: Stuart L. Meyer, Chicago; Jonathan I. Meyer, Evanston, both of IL (US); Eric S. Meyer, Princeton Junction, NJ (US); David M. Meyer, Chicago, IL (US)

(73) Assignee: Televideo Consultants, Inc., Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/366,156

(22) Filed: Aug. 3, 1999

Related U.S. Application Data

(63) Continuation-in-part of application No. 08/874,872, filed on Jun. 13, 1997, now Pat. No. 6,055,993, which is a continuation-in-part of application No. 08/387,350, filed on Feb. 13, 1995, now Pat. No. 5,678,579, which is a continuation-in-part of application No. 08/201,344, filed on Feb. 24, 1994, now Pat. No. 5,469,874.

(51) Int. Cl.[7] .................................................. A61C 15/00

(52) U.S. Cl. ........................ 132/323; 132/325; 132/326; 132/327

(58) Field of Search ..................... 132/323, 324, 132/325, 326, 327

(56) References Cited

U.S. PATENT DOCUMENTS

| D. 251,074 | 2/1979 | Schiff | D28/64 |
|---|---|---|---|
| 2,607,357 | 8/1952 | Talcott | 132/92 |
| 2,650,598 | 9/1953 | Rodesci | 132/91 |
| 3,393,687 | * 7/1968 | Whitman | 132/323 |
| 3,799,177 | * 3/1974 | Bragg | 132/326 |
| 4,050,470 | 9/1977 | Miller | 132/89 |
| 4,304,246 | * 12/1981 | Yafai | 132/323 |
| 4,519,408 | 5/1985 | Charatan | 132/89 |
| 4,982,752 | 1/1991 | Rodriguez | 132/327 |
| 5,086,792 | 2/1992 | Chodorow | 132/323 |
| 5,123,432 | * 6/1992 | Wyss | 132/323 |
| 5,199,452 | 4/1993 | Cheng | 132/325 |
| 5,224,501 | * 7/1993 | McKenzie | 132/323 |
| 5,327,977 | * 7/1994 | Lukashuk | 132/324 |
| 5,469,874 | * 11/1995 | Meyer et al. | 132/323 |
| 5,535,759 | 7/1996 | Wilk | 128/898 |
| 5,678,579 | * 10/1997 | Meyer et al. | 132/323 |

OTHER PUBLICATIONS

Partial European Search Report dated Jun. 30, 1999.
"Primary Preventive Dentistry," by Norman O. Harvis and Arden G. Christen, published by Appleton and Lange, East Norwalk, CT 06855 in 1991, *Personal Oral Hygiene*, pp. 108–117 and 118–123.
"Oral Hygiene Products and Places," by Morton Pader, published by Marcel Dekker, Inc., New York, New York 10015 in 1988, *The Toothbrush and Other Mechanical Devices*, pp. 178–194.

(List continued on next page.)

*Primary Examiner*—Pedro Philogene
(74) *Attorney, Agent, or Firm*—Richard G. Lione; Brinks Hofer Gilson & Lione

(57) ABSTRACT

An apparatus for moving a flexible comprises first and second elongated handles, each of the handles having at least an upper and a lower aperture defined therethrough, the apertures extending substantially transversely to the elongated handles. At least one central aperture is also defined in each of the first and second handles, the central aperture extending substantially transversely to the elongated handles and positioned between the upper and lower apertures. A loop of flexible element, extends through, and freely slidable within each of the apertures in each of the handles, wherein manipulation of the handles in conjunction with pressure applied to the loop of flexible element advances the element through the apertures to change the position of the flexible element relative to the handles.

22 Claims, 11 Drawing Sheets

OTHER PUBLICATIONS

Title and author unknown, believed to be published in U.S. before filing date of Feb. 13, 1995, pp. 440–445 with headings "Part Six Disease Prevention and Health Maintenance" and "Oral Health Strategies."

Title and author unknown, believed to be published in U.S. before filing date of Feb. 13, 1995, pp. 320–325 with headings "Prevention and Auxiliary Plaque Control Measures."

* cited by examiner

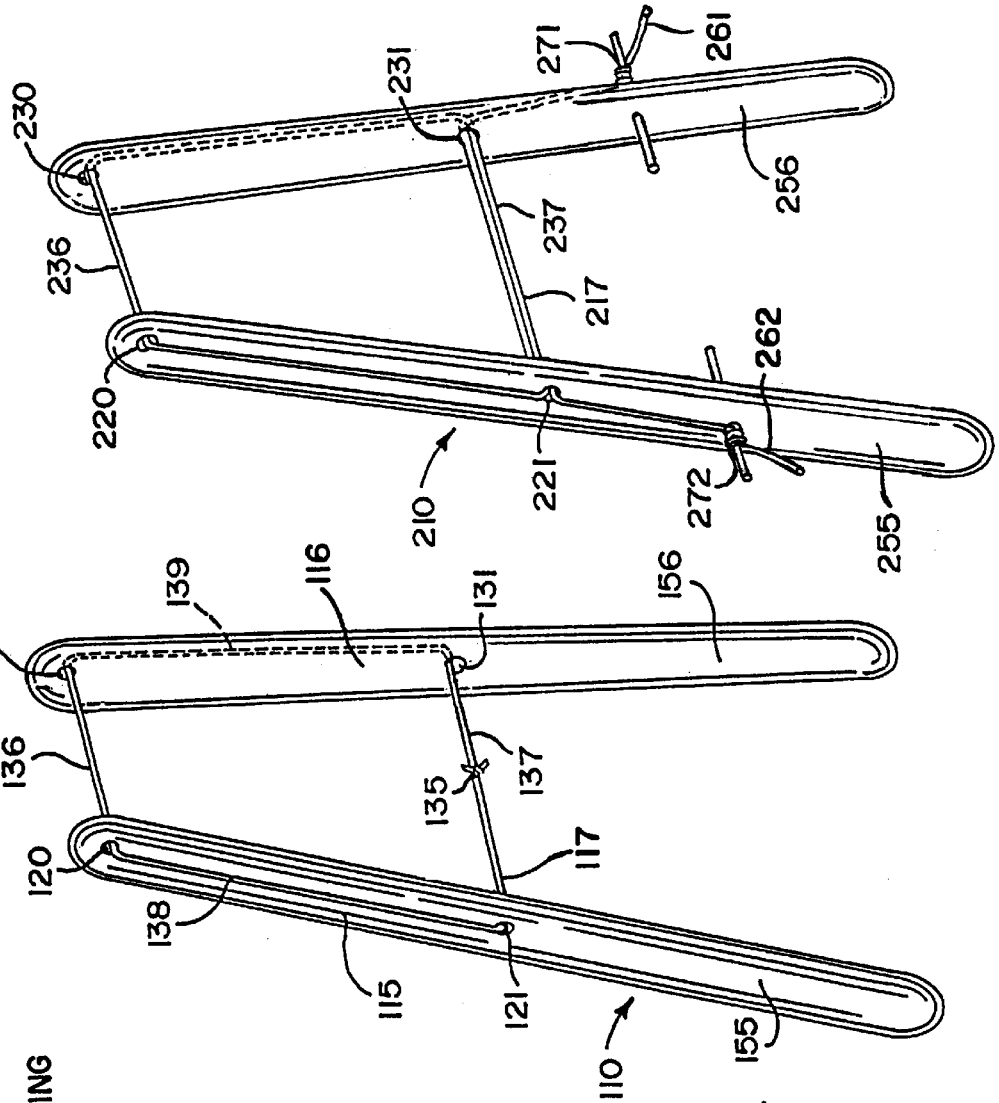

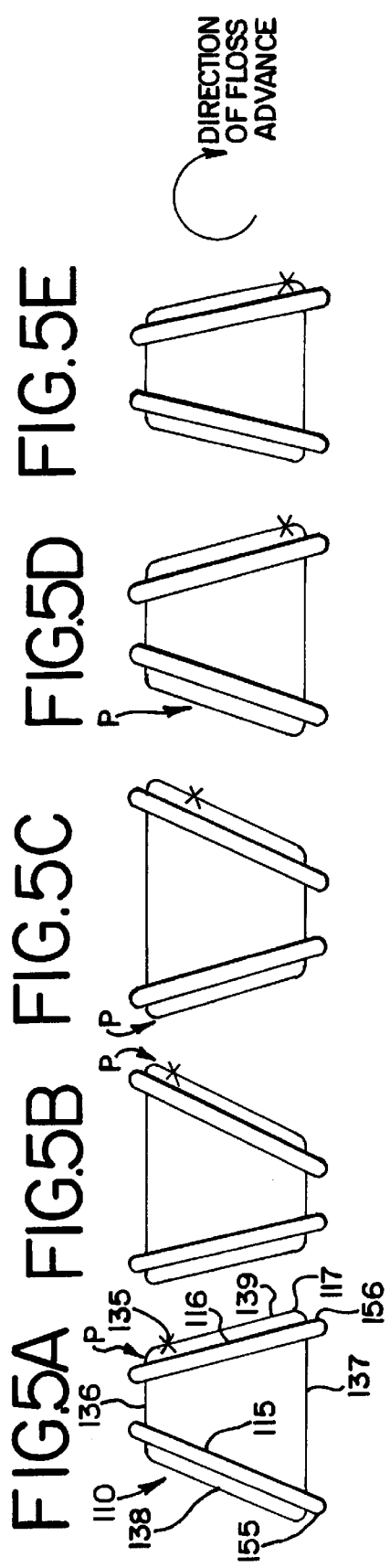
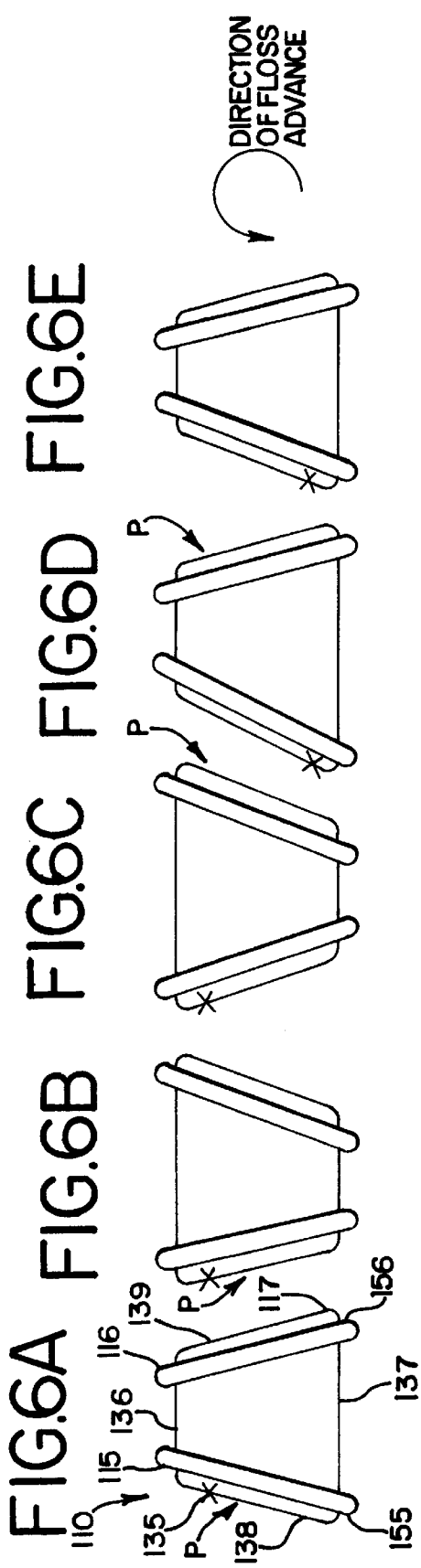

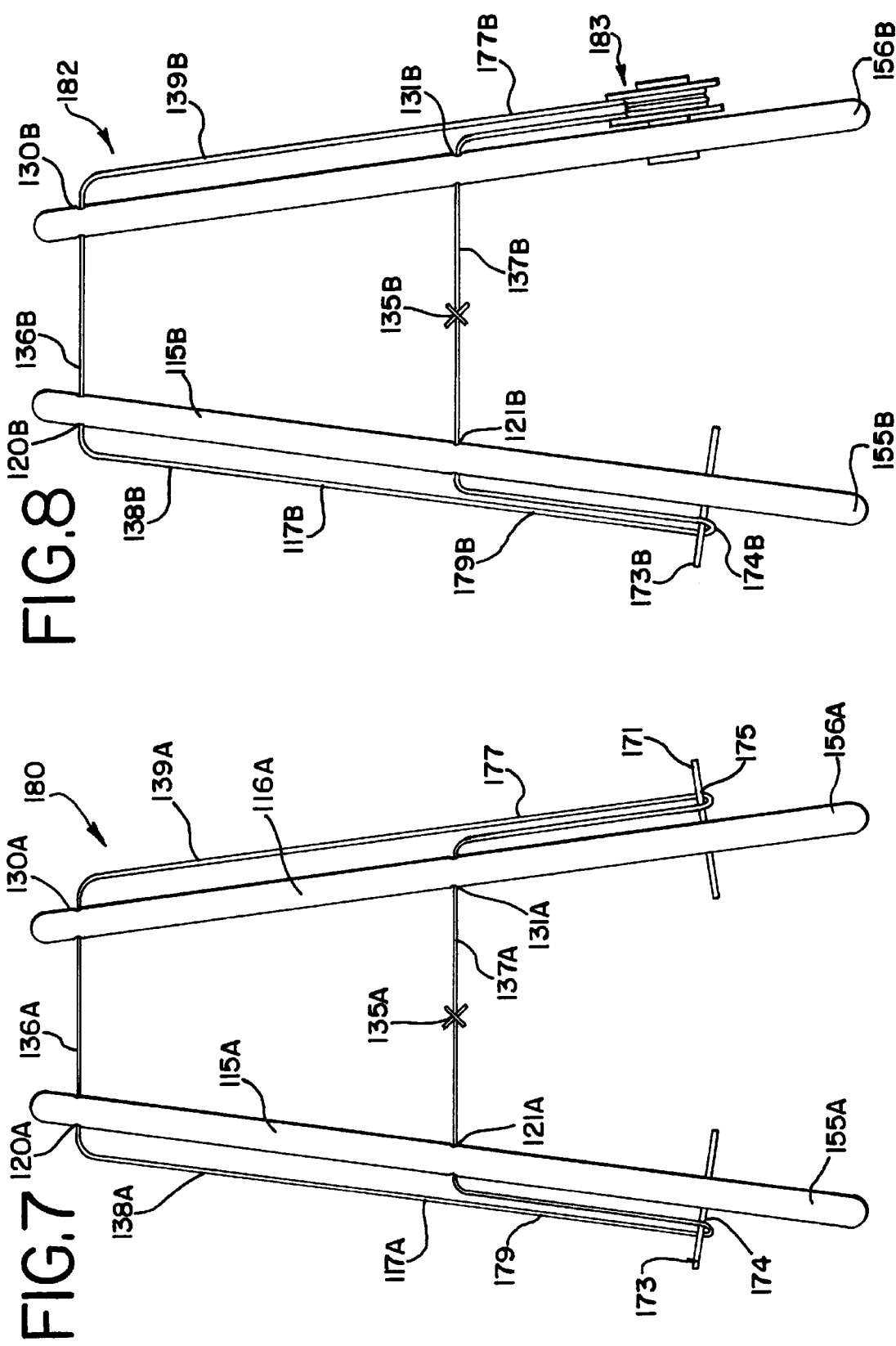

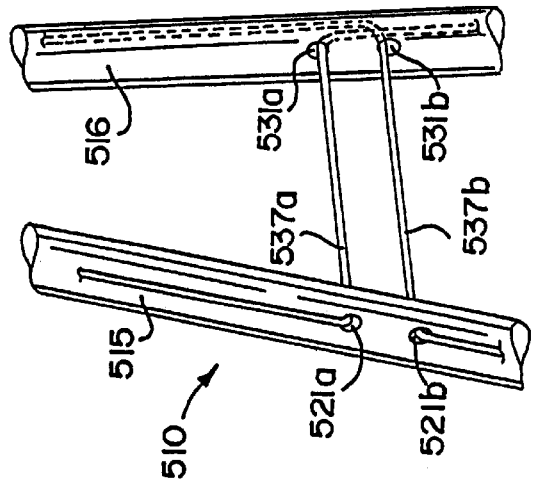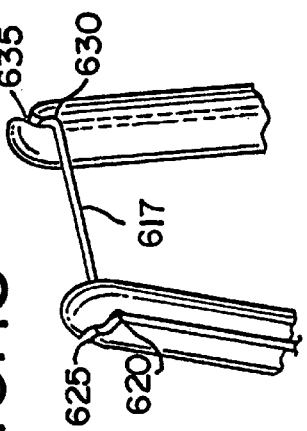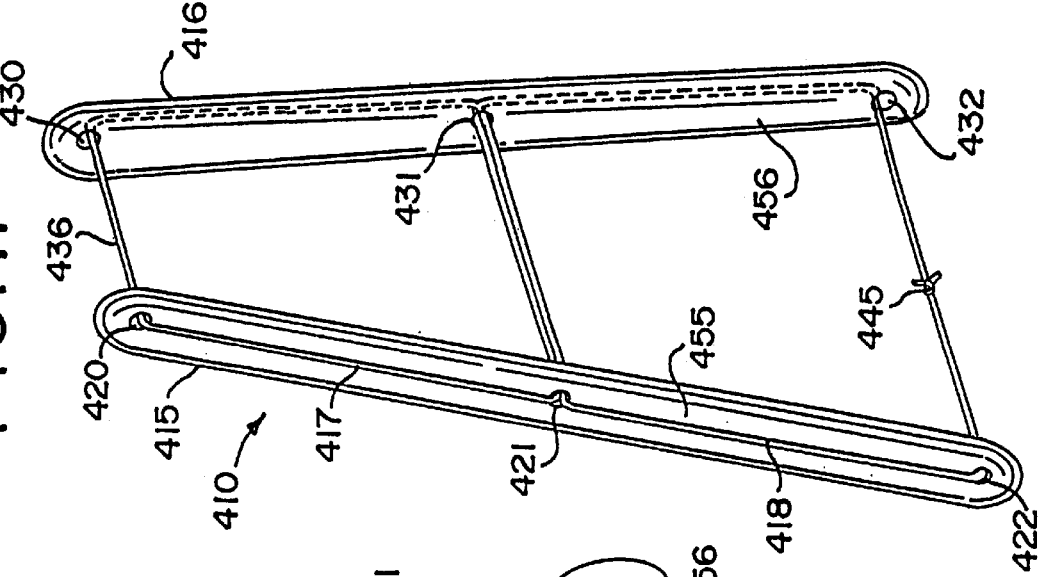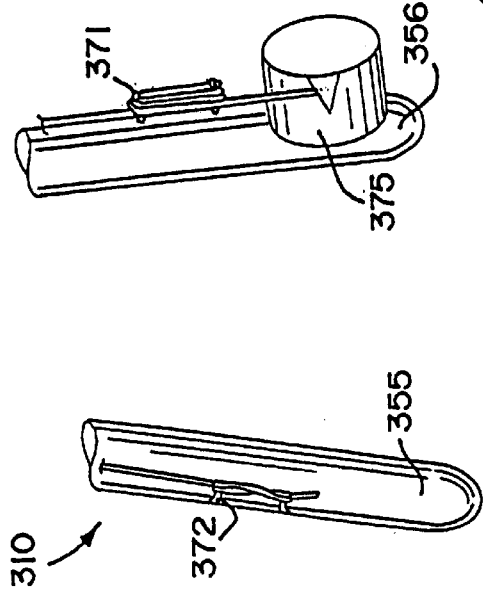

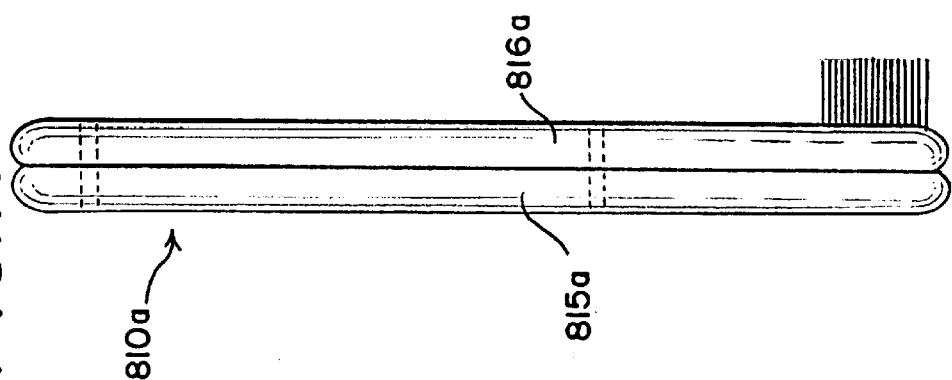
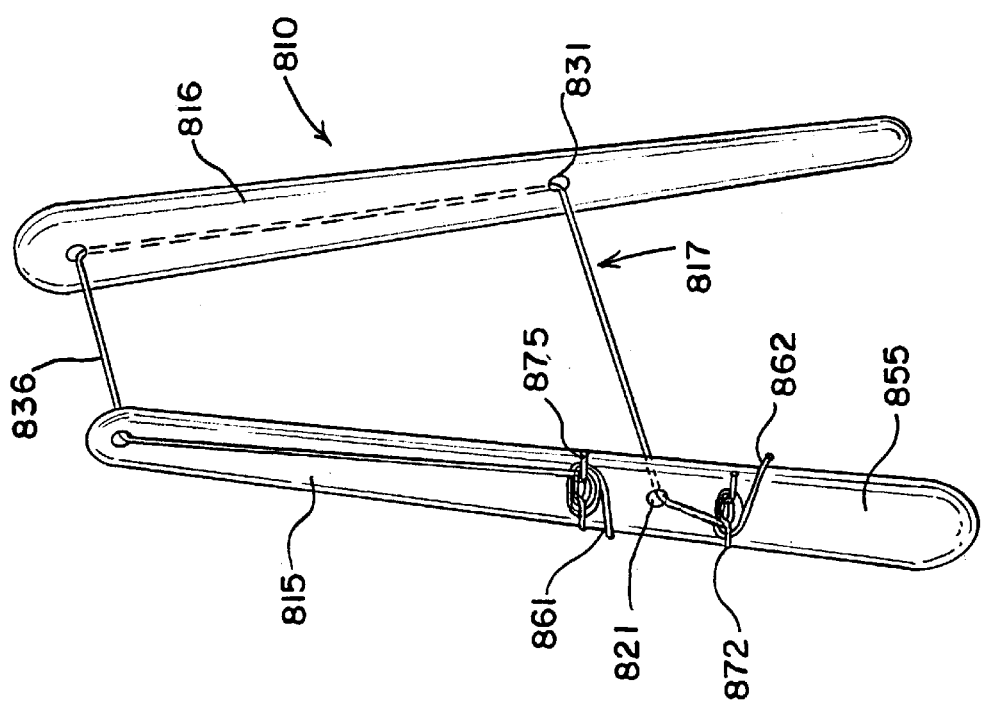
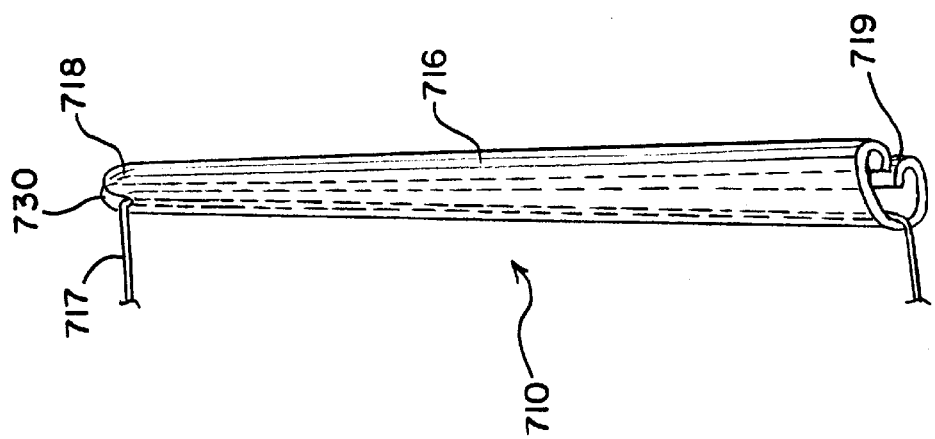

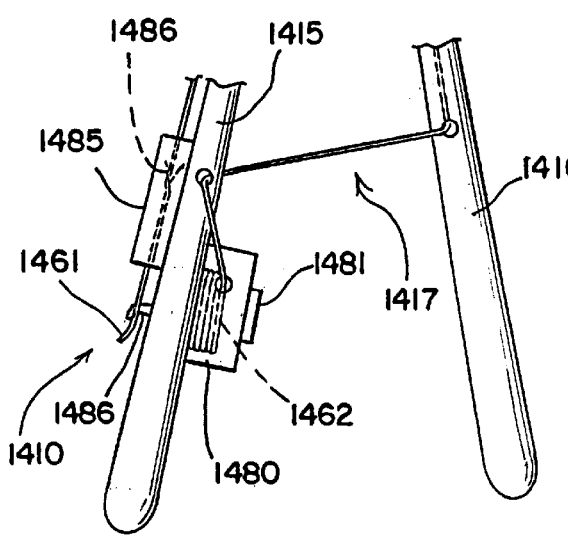
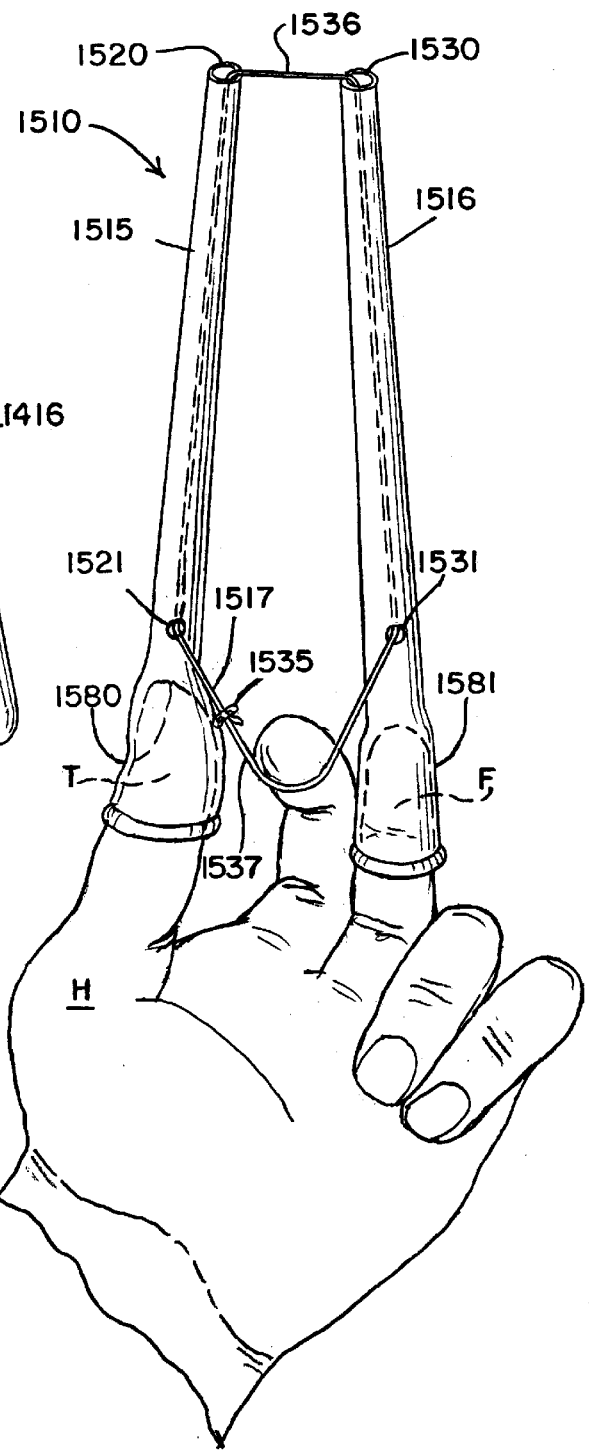

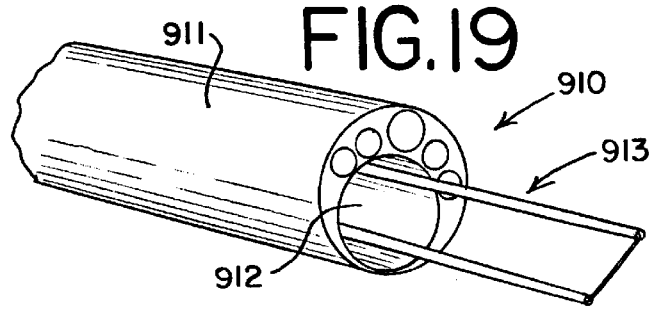
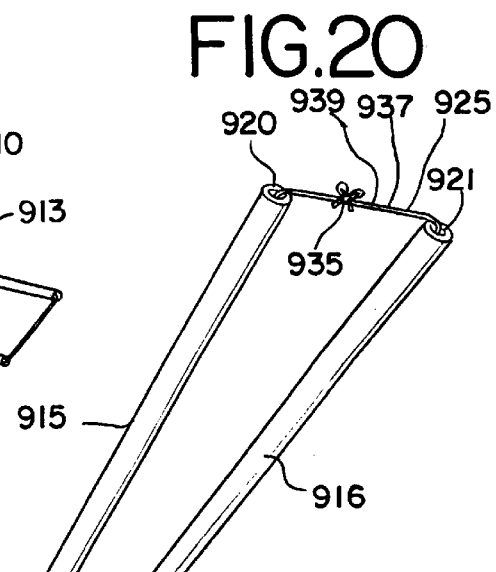
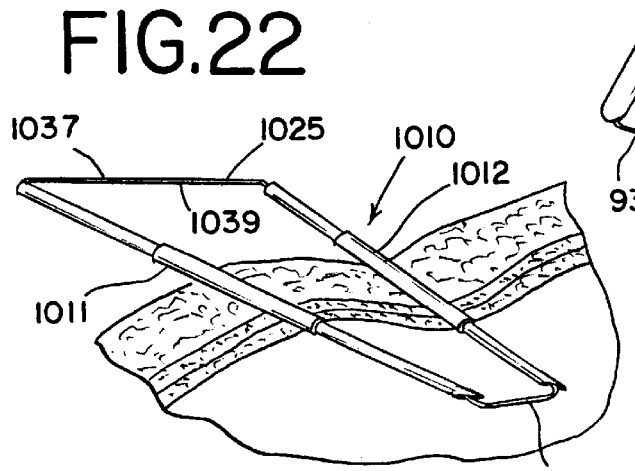
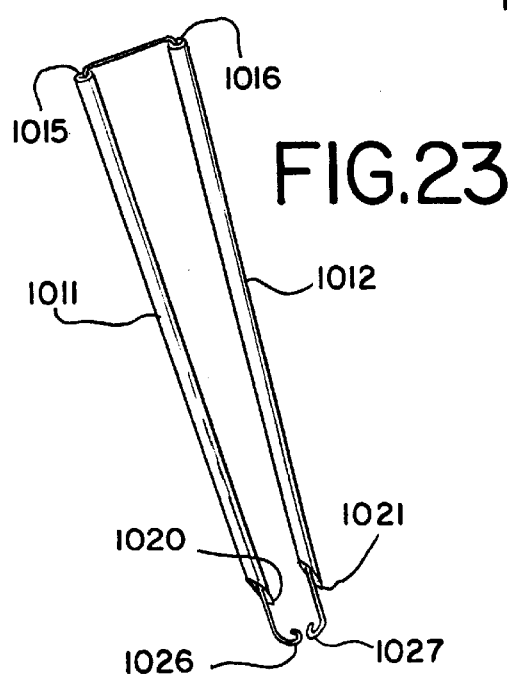
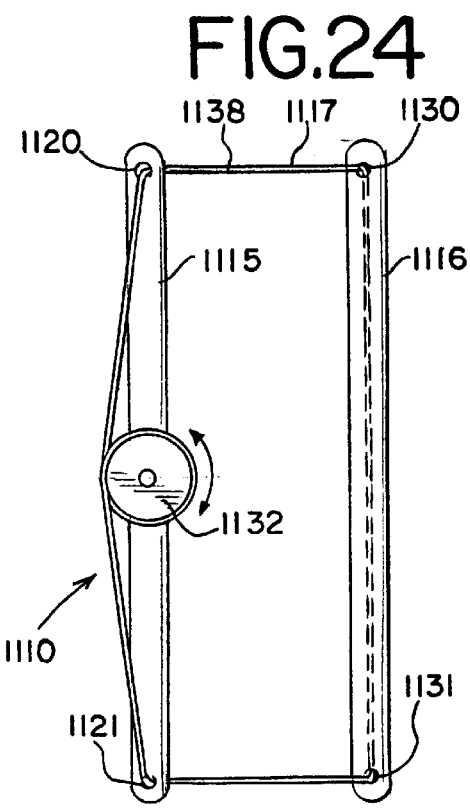

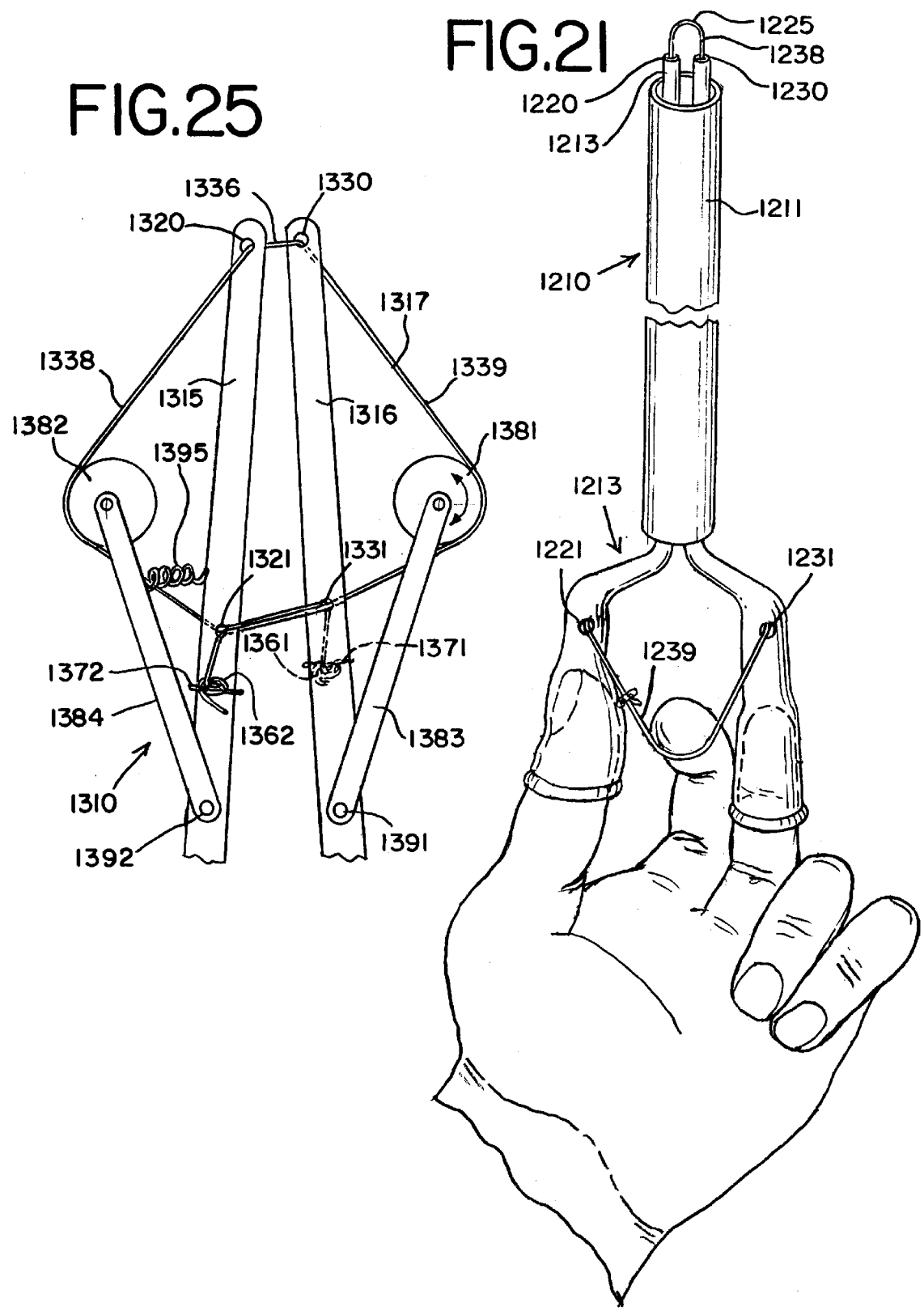

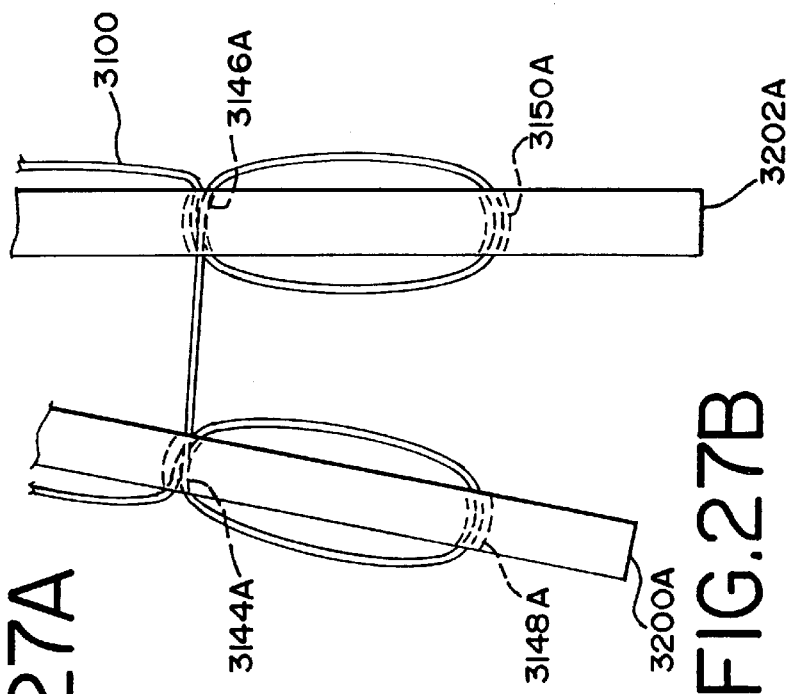
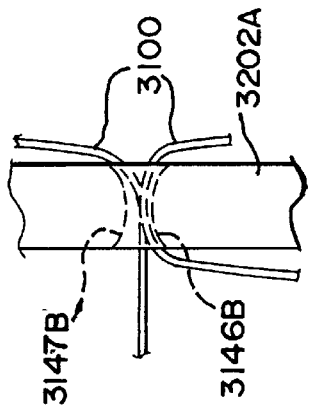
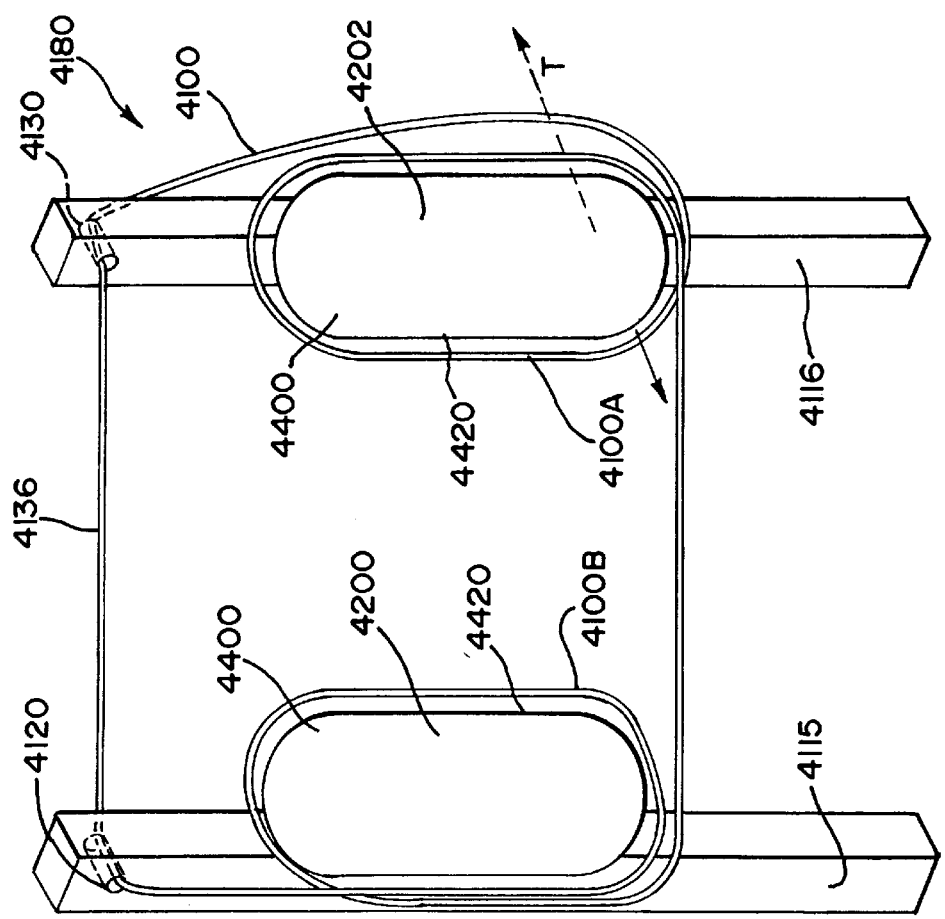

APPARATUS AND METHOD FOR POSITIONING AND MOVING A FLEXIBLE ELEMENT

RELATED APPLICATION

This application is a continuation-in-part of U.S. application Ser. No. 08/874,872, filed Jun. 13, 1997, now U.S. Pat. No. 6,055,993, which is a continuation in part of U.S. application Ser. No. 08/387,350, filed Feb. 13, 1995 entitled APPARATUS AND METHOD FOR POSITIONING AND MOVING A FLEXIBLE ELEMENT, now U.S. Pat. No. 5,678,579, which is in turn a continuation-in-part of U.S. application Ser. No. 08/201,344, filed Feb. 24, 1994, entitled APPARATUS AND METHOD FOR PERFORMING DENTAL FLOSSING, now U.S. Pat. No. 5,469,874.

FIELD OF THE INVENTION

This invention relates generally to an apparatus and method for positioning and moving a flexible element, e.g., a cord, wire or band, in space to use the element for performing various tasks. The tasks might be as diverse as dental flossing, laparoscopic surgery or mechanical sanding or abrading.

BACKGROUND OF THE INVENTION

It has long been known in the field of dental hygiene, for example, that it is important to remove food particles, tartar, and plaque from the teeth at least once a day. The removal of such dental contaminants may be accomplished by various means such as by brushing, water spray or the use of dental floss.

Dental floss is conventionally held in the hands and manipulated by the fingers. The floss is inserted between two adjacent teeth, or looped partially around a single tooth and pulled or pushed back and forth against the tooth to remove the food particles, tartar and plaque. This procedure requires a certain amount of manual dexterity and also requires the flosser to insert his or her fingers into the mouth.

A variety of mechanical devices have been developed to aid in the use of dental floss. Among these are devices consisting of a forked or U-shaped handle. In these devices a length of dental floss is tautly stretched between the two tines of a device. The device is manipulated from outside the mouth so as to draw the dental floss up and down against the surface of the tooth to be cleaned. Examples of such devices are found in Schiff U.S. Pat. No. Des 251,074 and the Yafai U.S. Pat. No. 4,304,246. In the latter, the floss is in the form of a loop which is stretched around the device.

In another flossing device, illustrated and described in the Wyss U.S. Pat. No. 5,123,432, parallel handles have a floss loop extending through them and interconnected across opposite ends. The handles are spaced at their mid-points by a spacer member which forms a fulcrum. The handles are manipulated by squeezing them at one end so that they pivot in a plane about the fulcrum and draw the floss tight at one end (the flossing end). In lieu of the spacer member illustrated, the handles may be manipulated in the same manner about a fulcrum formed by the flosser's finger.

In yet another flossing device, illustrated and described in the Braqg U.S. Pat. No. 3,799,177, the use of two separate handles is shown. A length of floss is stretched between the corresponding working ends of the handles and flossing accomplished by manipulating the other ends separately.

The above devices have shortcomings, however. First, the devices do not allow a continuous, movable loop of floss or other flexible element to be positioned or manipulated from any point in space. Furthermore, these devices do not allow the controlled manipulation of the floss element within the confines of very small volumes, such as in the rear of the mouth.

SUMMARY OF THE INVENTION

An object of the invention is to provide a new and improved apparatus for positioning and moving a flexible element in space to use the element for performing various tasks.

Another object is to provide an improved apparatus for dental flossing.

Still another object is to provide an improved flossing apparatus comprising a pair of independently controlled flossing handles which are interconnected only by a loop of floss.

Yet another object is to provide an improved dental flossing apparatus wherein segments of the floss loop which interconnect the handles are lengthened and shortened at will and in an endless variety of ways by manipulating the handles independently of each other.

Another object is to provide a flossing apparatus which can be effectively used while inserting only a minimal amount of the apparatus into the mouth.

Still another object is to provide a flossing apparatus which can readily be adapted to incorporate a store of floss.

Another object is to provide an improved dental flossing apparatus wherein a continuous loop of floss may be easily manipulated and advanced through a pair of independently controlled flossing handles.

Another object is to provide a low-cost, improved dental flossing apparatus that advances an integral loop of floss through a pair of independently controlled flossing handles.

Still another object is to provide an improved flossing apparatus which assists in positioning a working segment of floss easily within a deep oral cavity.

A further object provides a flossing apparatus which is simple and inexpensive to manufacture.

Another object is to provide an improved apparatus for performing laparoscopic surgery.

Another object is to provide an improved apparatus for performing mechanical sawing or abrading.

Various of the foregoing and other objects are realized in accord with one aspect of the present invention by providing an apparatus comprising a pair of separate and distinct handles which are interconnected by a loop of flexible elements such as a length of dental floss. The loop is formed from a length of element and includes a working segment which interconnects corresponding free ends of the handles, a control segment which interconnects the handles at points displaced from the free ends, and a pair of side segments which run along corresponding handles between respective ends of the working and control segments. The handles are free to move on all axes relative to each other, restrained only by the dimensions of the loop. They are also free to move relative to the loop.

In one embodiment of the apparatus, the handles are preferably of identical length. The loop passes through connecting apertures at opposite ends of each handle. Free ends of the element which form the loop are tied together or otherwise interconnected in the control segment (or side segments) of the loop.

In another embodiment of the apparatus, the handles are preferably of identical length but are considerably longer than those in the previously described embodiment. The handles each extend beyond the point where the control segment of the loop interconnects with the handles, thus providing handle extensions.

In a modification of the other embodiment, the single, continuous loop is replaced by a floss store mounted on one of the handle extensions. A loop is then effectively formed between the handles by passing it through the connecting apertures twice to form a control segment—in a manner hereinafter explained. The floss is then anchored adjacent the floss store, and the free end of the floss is anchored to the other handle extension.

In this modification, a variety of floss storing, cutting and anchoring mechanisms may be employed. For example, the floss store may be simply formed around a cleat. In the alternative, a container or spool of floss may be mounted on one handle extension.

As a further modification to this exemplary embodiment, a cleat may be formed or positioned on one or both of the handles to provide a retaining area for the "slack" of a single, continuous loop of floss as used in the first embodiment.

In another modification of this other, i.e., second embodiment of the flossing apparatus, a floss store is provided on one handle extension, anchored thereto. A loop is formed between the handles in a manner which will be hereinafter explained. The free end of the floss is then held and anchored on the aforementioned one extension while flossing is accomplished.

In a variation of this modification, the handle assembly accommodates an additional improvement. The other handle, which is now bare of cleats or the like, is provided with a bristle assembly at one end and, as a result, serves the dual function of a toothbrush and a flossing handle.

In yet another embodiment of the flossing apparatus, longer handles, i.e., handles which include extensions beyond the control segment of the floss loop are employed. The floss loop is continued to the free ends of the extensions where it passes through apertures thereon to form another loop. The result is a double floss loop or figure eight loop. This embodiment may be used advantageously with one hand; for example, by a handicapped flosser.

Other embodiments of the flossing apparatus invention are also disclosed. They will, of course, be described hereinafter in some detail.

In a method of the invention related to flossing, the flossing handles are normally used by manipulating them separately to achieve any optimum working floss segment length and angular relationship between the handles for the particular flossing operation contemplated. Only a short length of the apparatus is inserted in the mouth. The flosser applies pressure to the control segment of the floss, to the handles or to both handles and control segment to control pressure on the tooth being flossed.

In another method of the invention related to the manipulating a flexible element such as a loop of floss, the handles may be manipulated in such a fashion as to advance the loop of floss through the handles to provide "fresh" floss for the working segment while the apparatus is in use. The method involves, for example, alternately applying pressure to the floss segments against the handles and manipulating the handles back and forth to advance the floss, as will be explained in detail below.

In another aspect of the invention, a method and apparatus are provided for performing laparoscopic surgery. One embodiment involves the use of two rods carrying a loop of flexible wire through a single operating passage in a laparoscope. Another embodiment involves the manipulation of two laparoscopic tubes separately inserted into a patient. Each tube has a wire extending through it which, when advanced past the distal end of the tube inside the patient, can be connected by suitable means so as to form a loop. In either embodiment, manipulation of the loop within the patient by manipulation of the rods through one tube (the one embodiment) or the manipulation of rods through two tubes (the other embodiment) facilitates using the working segment of the loop for any of numerous tasks such as electrodissection, fulguration, coagulation, cutting, cautery or the like.

In yet another aspect of the invention, a method and apparatus are provided for mechanical cutting or abrasion. A pair of working handles mount a wire or band in the form of a loop. The wire or band loop is moved by driving the wire or band in one direction, or reciprocating it. The working segment of wire or band changes constantly and acts as an abrasive element for polishing jewels, for example. On a larger scale the working segment can function as a "chainsaw," in effect.

In one aspect of the present invention relating to an improved embodiment of the present invention, an apparatus for moving a flexible element is provided comprising first and second elongated handles, each of the handles having at least one aperture defined through an upper portion of the handles and a pair of lower apertures defined through a lower portion of the handles. A loop of flexible element is provided extending through each of the apertures, and spooling means is defined between the lower apertures on each of the lower portions for slidably retaining a portion of the loop of flexible element. The spooling means allows an extra portion of the element loop to be slidably stored on the handles, thereby allowing the user a greater store of floss from which to draw upon during use.

In another aspect of the present invention, an apparatus for moving a flexible element is described herein comprising first and second elongated handles, each of the handles having at least an upper and a lower aperture defined therethrough. The apertures extend substantially transversely to the elongated handles, and at least one central aperture is defined in each of the first and second handles, the central aperture extending substantially transversely to the elongated handles and positioned between the upper and lower apertures. A loop of flexible element is provided extending through and freely slidable within each of the apertures in each of the handles. Manipulation of the handles in conjunction with pressure applied to the loop of flexible element advances the element through the apertures to change the position of the flexible element relative to the handles.

BRIEF DESCRIPTION OF THE DRAWINGS

The invention, including its construction and method of operation, as well as additional advantages thereof, is illustrated more or less diagrammatically in the drawings, in which:

FIG. 3A is a vector diagram illustrating certain features of the invention;

FIG. 3B is an illustration of the vector diagram of FIG. 3A on a three-axis (X, Y, Z) graph;

FIG. 4 is a view, similar to FIG. 1, illustrating a second form of flossing apparatus embodying features of the present invention;

FIGS. 5A–5E comprise a schematic illustration of the apparatus shown in FIG. 4, illustrating a method for using the apparatus embodying features of the present invention;

FIGS. 6A–6E comprise a schematic diagram similar to that shown in FIGS. 5A–5E, illustrating an alternate method of using the flossing apparatus embodying features of the present invention;

FIG. 7 is a view, similar to FIG. 4, illustrating a modification of the flossing apparatus of FIG. 4 embodying features of the present invention;

FIG. 8 is a view, similar to FIG. 7, illustrating a modification of the flossing apparatus of FIG. 7 embodying features of the present invention;

FIG. 9 is a view, similar to FIG. 3, illustrating a modification of the second form of flossing apparatus;

FIG. 10 is a view, similar to FIG. 3, illustrating another modification of the second form of flossing apparatus;

FIG. 11 is a view, similar to FIG. 1, illustrating a third form of flossing apparatus embodying features of the present invention;

FIG. 12 is a perspective view of a variation on the flossing apparatuses shown in FIGS. 9, 10 and 11.

FIG. 13 is a perspective view of a variation on the flossing apparatuses shown in the preceding FIGURES;

FIG. 14 is a perspective view of another variation of the flossing apparatuses shown;

FIG. 15 is a perspective view of the flossing apparatus shown in FIG. 9;

FIG. 16 is a perspective view FIG. 15 apparatus, further modified;

FIG. 17 is a perspective view of another variation of the flossing apparatus shown in FIG. 9;

FIG. 18 is a perspective view illustrating a fourth form of flossing apparatus embodying features of a variation of the present invention;

FIG. 19 is a perspective view of a first form of laparoscopic surgery apparatus embodying features of the invention;

FIG. 20 is a perspective view of the rod and loop sub-assembly from the apparatus of FIG. 19;

FIG. 21 is a perspective view of another rod and loop subassembly for the apparatus of FIG. 19;

FIG. 22 is a perspective view of a second form of laparoscopic surgery apparatus embodying features of the invention;

FIG. 23 is an enlarged view of the working segment of loop in the second form of apparatus shown in FIG. 19;

FIG. 24 is a perspective view of a first form of mechanical sawing or abrasion apparatus embodying features of the invention;

FIG. 25 is a perspective view of a second form of a mechanical sawing or abrasion apparatus.

FIG. 28 is a perspective view of a variation of the flossing apparatus of FIGS. 26 and 27 incorporating the present invention.

DESCRIPTION OF THE PREFERRED EMBODIMENTS

Figure 1:
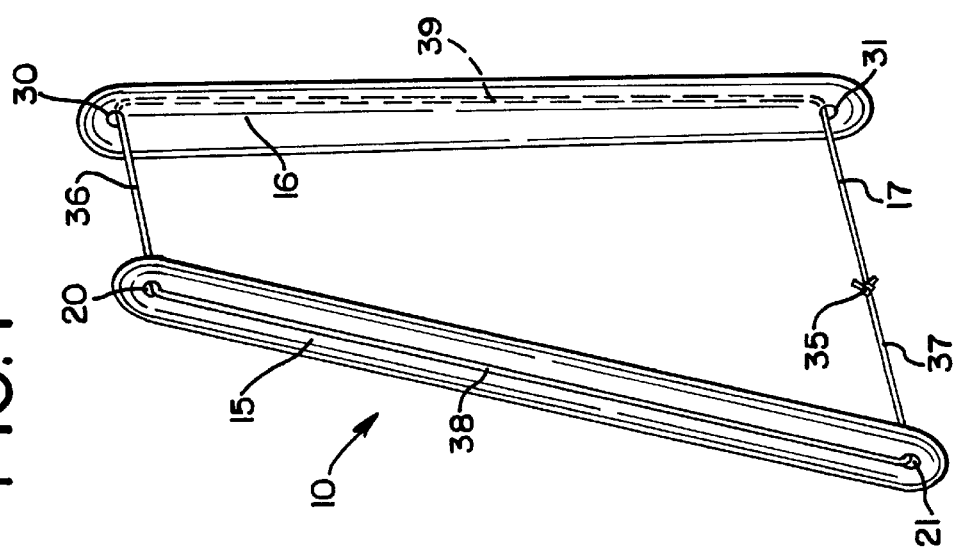
FIG. 1 is a perspective view of a first form of flossing apparatus embodying features of the present invention.

Referring now to the drawings, and particularly to FIG. 1, a flossing apparatus embodying a first form of the present invention is seen generally at 10. While most of the exemplary embodiments described below relate to a dental flossing apparatus, it is intended that the described invention is applicable to a variety of uses wherein a flexible element is required to be manipulated with accuracy and convenience. The apparatus 10 as shown comprises a pair of identical handles 15 and 16 interconnected by a loop 17 of flexible element such as a loop of conventional dental floss.

The handles 15 and 16 are each preferably about three inches long. Each is preferably formed of molded plastic, although wood, bamboo or any one of many different materials could be used. The handles 15 and 16 as shown each have a circular cross-section, with a diameter of about one-quarter inch. The dimensions and shapes described are not critical to the invention, however, and may be varied without obvious limits.

Small apertures 20 and 21 are formed transversely through opposite ends of the handle 15. Identical apertures 30 and 31 are formed through corresponding opposite ends of the handle 16.

A piece of dental floss preferably nine and one-half inches long is threaded through the apertures 21, 20, 30 and 31, and its free ends are tied together at a knot 35 to form the loop 17. With the apparatus 10 assembled in this way, the loop 17 is effectively divided into four segments, a floss working segment 36 between the apertures 20 and 30, a control segment 37 between the apertures 21 and 31, and a pair of side segments 38 and 39 paralleling corresponding handles 15 and 16.

The apparatus 10 is illustrated in FIG. 1 in its normal operating configuration. The handles 15 and 16 are inclined toward each other at the handle ends which carry the working segment 36 of the loop 17 between them. They are inclined in such a way that the working segment 36 is between one-quarter inch and one inch long. The opposite ends of the handles 15 and 16 have the control segment 37 of the loop 17 between them. The control segment 37 is then between about three and one-quarter inches and two and one-half inches long. In this operating configuration the handles 15 and 16 would also normally be arranged so as to be non-coplanar.

Figure 2:
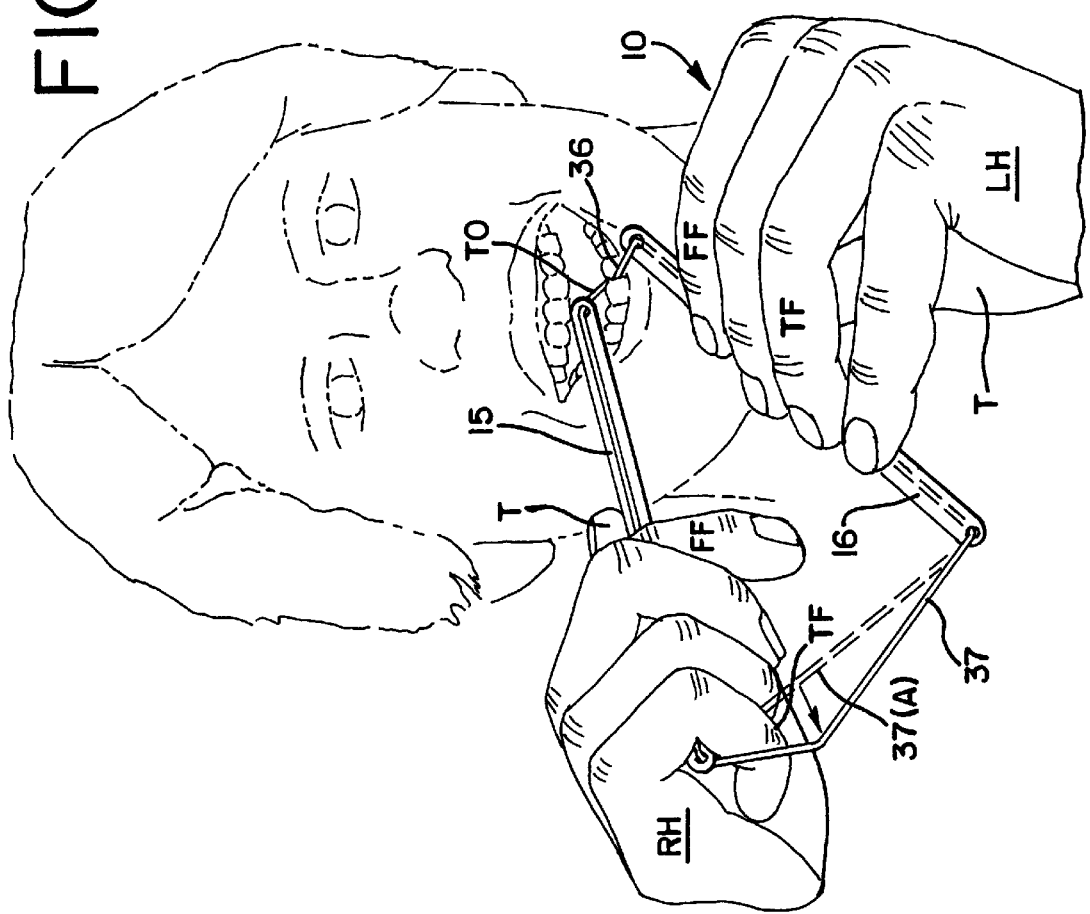
FIG. 2 is another perspective view of the first form of flossing apparatus, illustrating the method of the invention employed in properly flossing with the apparatus.

Referring now to FIG. 2, the flossing apparatus 10 is shown in the hands RH and LH of the flosser as it is used according to the method of the invention. The handles 15 and 16 are grasped between the thumb T and forefinger FF of the right hand RH and the left hand LH, respectively. The third, or other finger TF of one or both hands is then placed over or under the control segment 37 of the floss loop 17.

The flosser then inserts the working segment 36 of the floss loop 17 into position in front of or behind a tooth, or around a tooth (as shown). The handles 15 and 16 can be disposed in any angular relationship to each other in order to place the working segment 36 in the most advantageous position for each flossing operation, and the operation performed by changing that angular relationship or while maintaining it. Flossing pressure is applied by the third, or other finger(s) TF of the flosser's hands pushing or pulling on the control segment 37 of the floss loop 17. As shown in the FIG. 3, the control segment 37, when pulled away from its position shown at 37A, becomes an operating segment for further control of the working segment 36 and handles 15 and 16. In the alternative, this flossing pressure can also be maintained by tilting (pushing or pulling) the handles away from each other at the control segment. In either case, the sum of the length of the control segment 37 and the working segment 36 remains constant throughout the manipulation of the handles or the control segment 37.

In geometry terms, the vectors defined by the two handles 15 and 16 can be deployed in such fashion as to be linearly independent of each other. That is, the handles 15 and 16 can be deployed in space in such fashion that their vectors never meet, if extended, even when they are not parallel. The loop 17 that is formed by floss passing through the apertures in the handles can, in fact, be non-planar. This confers more degrees of freedom on the handles 15 and 16 and the loop segment 36 at the business end of the handles. This is very different from prior art flossing implements. They are not only coplanar, usually being configured in a "fork" geometry, but the plane of the floss segment and the plane of the arms or handles are normally coupled rigidly.

The mathematical expression of this relationship in the present invention illustrates the distinction between the present invention and the prior art. Referring now to the illustration of FIG. 3, consider one handle 15 to be a directed line segment called VECTOR, $\vec{V}_A$, where the other handle 16 is a directed line segment called VECTOR, $\vec{V}_B$. The working segment 36 of the floss is also a directed line segment called VECTOR, $\vec{V}_{WORKING}$, where the size of the segment can vary. The control segment 37 of the floss is not independent, since $\vec{V}_{CONTROL\ SEGMENT}$ is defined by the relation:

$$\vec{V}_{CONTROL\ SEGMENT} = \vec{V}_A - \vec{V}_B - \vec{V}_{WORKING\ SEGMENT}$$

(this, of course, is why the $\vec{V}_{WORKING\ SEGMENT}$ is determined by $\vec{V}_A$, $\vec{V}_B$ and $\vec{V}_{CONTROL\ SEGMENT}$). The coplanarity (linear dependence) relation is thus defined by $$[\vec{V}_A \times \vec{V}_B] \cdot \vec{V}_{WORKING\ SEGMENT} = 0,$$

where the vector operators indicate VECTOR CROSS PRODUCT and VECTOR DOT PRODUCT, respectively. The NON-COPLANARITY CONDITION, which is a feature of the present invention, is defined by $$[\vec{V}_A \times \vec{V}_B] \cdot \vec{V}_{WORKING\ SEGMENT} \neq 0.$$

Why is this relationship important?. The object of using a tool to deploy floss segments within the mouth is to avoid having to distend the mouth unduly, or to trigger a gag reflex, or to insert non-hygienic fingers, or to insert fingers encased in latex, which has the disadvantage of tasting bad, smelling unpleasant and triggering allergic reactions to latex. This means that the floss segment should be deployable without having to change the orientation of the handles, point for point. The degrees of freedom inherent in the present invention allow the apparatus to move relatively little inside the mouth while permitting complete flexibility in deploying the working floss segment. There should be as little of the apparatus in the mouth as possible, aside from the floss segment.

In the present invention, the working floss segment is variable in length, as well as orientatable in space. The apparatus allows the working floss segment to be long or short, at will. It also allows the floss working segment to be taut, or slack, by itself, or pulled around a tooth or pushed against a tooth. That is, the floss working segment can be put under tension in either a line segment (when inserting between teeth) or in a curvilinear arc convex to the front of the mouth (when pushing against the tooth) or concave to the front of the mouth when pulling against a tooth.

Referring now to FIG. 4, a flossing apparatus embodying a second form of the present invention is seen generally at 110. The apparatus 110 is, in many respects, identical in construction to the flossing apparatus 10 hereinbefore discussed. To the extent that components are identical, corresponding reference numerals, plus one-hundred digits, are used.

As seen in FIG. 4, a floss loop 117 is mounted on a pair of identical flossing handles 115 and 116 by passing it through apertures 120 and 130 on corresponding ends of the handles and apertures 121 and 131 spaced about three inches from corresponding apertures 120 and 130. The loop 117 is knotted at 135 and includes a working segment 136, an operating segment 137 and side segments 138 and 139.

Unlike the apparatus 10, however, the handles 115 and 116 have handle extensions 155 and 156 below the apertures 121 and 131. These extensions 155 and 156 are each approximately four inches long, making the handles 115, 155 and 116, 156 each about seven inches long. This configuration of the flossing apparatus 110 permits the flosser to grip the handle extensions 155 and 156 and manipulate the working segment 136 of the floss from a point further removed from the mouth. All of the advantages of the apparatus 10 are retained.

Referring now to FIG. 5, a schematic diagram shows the apparatus 110, including handles 115 and 116, working segment 136, control segment 137 and side segments 138 and 139 on the floss loop 117. The progression of schematic FIGS. 5A–5E show one of the particular benefits of the present invention, in that the floss loop 117 may be advanced through the apertures in the handles 115 and 116 and around the apparatus 110 to provide "fresh" floss for working segment 136. This ability to advance the floss may be seen by observing the knot 135 throughout the progression of FIGS. 5A–5E. In FIG. 5A, the floss loop 117 is tensioned with the handles 115 and 116 oriented as shown. Pressure P is applied to the side segment 139 by pressing the user's finger against the side segment 139 to hold side segment 139 against the outside of handle 116. Note that the position of the handles 115 and 116 are such that the length of the working segment 136 is less than the length of the control segment 137.

The handles 115 and 116 are then moved apart so that the length of the working segment 136 is longer than the length of the control segment 137 as shown in FIG. 5B. Note the position of the knot 135. During this movement, pressure is maintained (as indicated by the arrow and the letter P) against side segment 139 to hold it against handle 116. Pressure is next applied to the opposing handle 115 as shown in FIG. 5C. As indicated by the arrow, pressure is applied to the side segment 138 to hold segment 138 against the handle 115. While maintaining this pressure, the handles 115 and 116 are moved into the position shown in FIG. 5D so that the length of the working segment 136 is again shorter than the length of the control segment 137. During this movement, note that the position of knot 135 (and therefore the loop 117) shifts to the position shown in FIG. 5D. Pressure may now be released as shown in FIG. 5E and the apparatus 110 may be used to continue flossing with a fresh working segment. The movements illustrated in FIGS. 5A–E advance the floss loop 117 in a clockwise direction. Such movements may be repeated to advance the floss further through the apparatus 110.

Referring now to FIGS. 6A–E, the same apparatus 110 is shown, but the schematic illustration for advancing the floss in the counter-clockwise direction is shown. These movements as illustrated in FIGS. 5A–E and 6A–E are useful to provide a flossing apparatus that contains an amount of floss sufficient for flossing an entire mouthful of teeth. This relatively simple apparatus will not waste any extra floss, and the relatively simple construction would preferably allow such an apparatus to be inexpensive and disposable.

Referring now to FIG. 7, a modification of the above flossing apparatus is illustrated at 180. The apparatus 180 is, in most respects, identical to the flossing apparatus 110 hereinbefore discussed. To the extent that the components are identical, corresponding reference numerals, plus the letter designation "A", are used.

As shown in FIG. 7, a longer floss loop 117A is threaded through the apertures 120A, 130A, 121A, and 131A. Thus, the overall length of the floss used for the loop 117A is longer than the length used for the floss loop 117 in the previous figures. The extra length comprises a slack portion 179 and 177 which is retained in proximity to the handle extensions 155A and 156A by a cleat 173 and 171 preferably mounted transverse to each of the handle extensions 155A and 156A. Each cleat 173 and 171 preferably includes a cylindrical peripheral surface 174 and 175, respectively, to allow the slack portion 179 and 177 of the loop 117A to be tensioned along with the side segments 138A and 139A. When the handles 155A and 116A are moved apart to tension the loop 117A, the loop acts in a similar fashion to the simple loop 117 illustrated in FIG. 4.

Furthermore, the embodiment shown in FIG. 7 allows the user to manipulate the handles 115A and 116a in a fashion similar to that shown in FIGS. 5 and 6 above to advance a larger loop of floss through the apertures. The larger floss loop would be desirable, for example, where the user would require more floss to complete the flossing of a particular set of teeth. The cleats 173 and 171 allow a larger loop of floss 117A to be used, and also allow the user to apply pressure to the side segments 138A and 139A by simply pressing on the slack portions 179 and 177, respectively, which are closer to the handle extensions on apparatus 180.

FIG. 7 illustrates the slack portion 179 and 177 of the loop 117A entrained around the cleats 173 and 171 in a single turn. If desired, the user can create more friction to hold the slack portions 179 and 177 more securely by wrapping the portions 179 and 177 around the cleats 173 and 171, respectively, more than once. The friction force holding the slack portions 179 and 177, and thus the side segments 138A and 139A, is similar to the force used to hold a boat to a dock using a dock-mounted bollard.

Referring now to FIG. 8, a modification of the above flossing apparatus is illustrated at 182. The apparatus 182 is, in most respects, identical to the flossing apparatus 180 hereinbefore discussed. To the extent that components are identical, corresponding reference numerals, plus the letter "B", are used.

As seen in FIG. 8, a rotatable floss spool 183 is mounted to the handle extension 156B. The spool 183 may be used to contain a somewhat larger excess, or slack, of floss from a very large loop 117B of the floss. Again, as illustrated in the schematic drawings of FIGS. 5 and 6, the floss may be advanced through this apparatus in a similar fashion. It should be noted that the loop 117B is a true, continuous loop, the excess of which is wound around the spool 183 without breaking the loop. This feature may allow, for example, the apparatus 182 to contain enough floss slack in the loop 117B to provide renewable floss at the working segment 136B for many days.

Alternatively, the rotatable spool 183 can consist of a takeup portion which winds up the used floss, and a storage portion, which unreels fresh floss in such fashion that the used floss and the fresh floss do not touch and which allows the floss to be not necessarily a continuous loop but, rather, anchored respectively used floss on the takeup/windup portion and the fresh floss on the unwind portion of the spool. Preferably, if the floss breaks, or one wishes to discard the used floss, fresh floss can be unwound and the distal end anchored on the takeup portion.

The rotatable spool can preferably be subject to a brake or allowed to rotate so long as the used and fresh floss act as a fixed length continuous loop.

Referring now to FIG. 9, a modification of the above flossing apparatus is illustrated at 210. The apparatus 210 is, in most respects, identical to the flossing apparatus 110 or 180 hereinbefore discussed. To the extent that components are identical, corresponding reference numerals, plus one-hundred digits, are used.

As seen in FIG. 9, rather than being knotted at opposite free ends to form a loop, the loop 217 is formed by passing opposite ends 261 and 262 of the piece of floss through both apertures 221 and 231, in opposite directions. One end 261 is then wrapped numerous times around a preferably transverse cleat 271 on the handle extension 256 to form an anchored store of floss. The other end 262 is wrapped around a similar cleat 272 on the handle extension 255 to anchor it there. The cleats 271–272, of course, may be of any shape, and not necessarily symmetrical on both sides as shown.

By passing the opposite ends of the floss element through apertures 221 and 231 in this fashion, a "virtual loop" is formed. In other words, even though opposite ends 261 and 263 of the piece of floss are not tied together, a "virtual loop" is created. This permits the floss element to be manipulated by the handles in the same fashion as the embodiment of apparatus 110 or 180. In this arrangement, the "virtual loop" also behaves similarly to the embodiment of apparatus 110 and 180 in that, by manipulating the handles, the working segment 236 may be lengthened or shortened while correspondingly shortening or lengthening a pair of overlying control segments 237. As described in detail below, and in relation to other embodiments, this "virtual loop" feature of the invention in the present embodiment allows for the attachment of a thread storing device or other means to one or more of the handles.

The second form of flossing apparatus 210 is employed using the same method described with relation to the apparatus 110. As will be seen, however, it is not necessary to remove and replace the floss loop 217 after use. Floss is simply unwound from the store 261 on the cleat 271 for an inch or two and pulled through the apertures 231, 221, 220, 230, 231 and 221, in that order. The floss is then anchored again at the cleat 272, after which the excess can be cut off. This permits a very frugal use of floss since, for a single user, only one inch of new floss is needed for each "freshening". Alternatively, a completely pristine nine to ten inches of floss can be withdrawn for a new use and the excess discarded. An unused working segment 236 of floss is then in position.

Referring now to FIG. 10, another modification of the second form of flossing apparatus is illustrated at 310 (only the handle extensions 355 and 355, corresponding to the extensions 255 and 255 in FIG. 9, are shown). In the apparatus 310, a mounting receptacle 375 is affixed to the handle extension 356 and, in this receptacle, a standard small-size floss capsule 376 is removable mounted.

Floss is drawn from the capsule 376 and threaded through handle apertures in the manner illustrated in FIG. 9. When sufficient floss to reach and go well past an anchor cleat 372 on the handle extension 355 has been reached, the floss at the capsule 376 is placed under the conventional anchor cleat 371 associated with it. The free end is then anchored onto the cleat 372.

With regard to the aforedescribed modifications of the second embodiment, a wide variety of floss storage and anchoring mechanisms could be used. In addition, where such storage capability is provided, a floss cutting mechanism on the handle extension opposite the storage mechanism is preferably incorporated.

Referring now to FIG. 11, a flossing apparatus embodying a third form of the present invention is seen generally at 410. The apparatus 410 is, in many respects, identical in construction to the flossing apparatus 110 hereinbefore discussed. To the extent that components are identical, corresponding reference numerals, plus three-hundred digits, are used.

As seen in FIG. 11, the floss loop 417 is only part of a larger, double-loop 417, 418. The lower loop 418 is formed by crossing the ends of the length of floss through the apertures 421 and 431 and extending hose ends downwardly along the handle extensions 455 and 456 to apertures 422 and 432 in corresponding extensions. The ends of the floss segment are then passed downwardly through the apertures 422 and 432 and tied together at a knot 445.

With this configuration apparatus 410, flossing can be done easily with one hand. The handle extensions 455 and 456 are gripped between fingers of one hand, somewhat like chopsticks, and the position, length and pressure applied by the floss working segment 436 controlled in this way.

Referring now to FIG. 12, a variation of the apparatuses 210, 310 and 410 hereinbefore discussed is seen in the flossing apparatus 510 (partially shown). It amounts to the creation of a spaced pair of apertures 521A, 521b and 531A, 531B in each of the handles 515 and 516. In forming the control segment 537 of the floss, the floss ends are threaded in opposite directions through the upper set of apertures 521A, 531A and the lower set 521B, 531B, respectively. Upper and lower floss control segments 537A and 537B are, thus, formed.

Referring now to FIG. 13, a variation of all the apparatuses hereinbefore discussed is seen in the flossing apparatus 610 (partially shown). It has slots 625 and 635 leading into corresponding apertures 620 and 630 through the handles 615 and 616. The slots 625 and 626 are duplicated adjacent corresponding other apertures through the handles (not shown) at their opposite ends. This slot construction permits preformed or pretied loops of floss 617 to be mounted on the handles by sliding them through corresponding slots into related apertures.

Referring now to FIG. 14, another variation of apparatuses hereinbefore discussed is seen in the flossing apparatus 710 (partially shown). It comprises a pair of identical handles, but only one is shown, at 716. The handles are each formed with a bullet-shaped tip 718 at its working end. As seen at the opposite (lower) end in FIG. 14, each handle 716 is formed so that a slot 719 extends along its length, with inwardly curled edges 723 of the handle forming the slot. The slot 719 extends across the top of the tip 718 to form an aperture 730 in the tip for the floss 717. This construction also permits preformed or pretied loops of floss to be easily mounted and retained.

Referring now to FIG. 15, yet another modification of the second form of flossing apparatus is illustrated at 810. The apparatus 810 is, in most respects, identical to the flossing apparatus 210 hereinbefore discussed. To the extent that components are identical corresponding reference numerals, plus six-hundred digits, are used.

As seen in FIG. 15, rather than being knotted at opposite free ends to form a loop, the loop 817 is formed by passing one end 862 of the piece of floss through both apertures 831 and 821, in that order. The end 862 is then wrapped numerous times around a transversely oriented cleat 872 on the handle extension 855 to form an anchored store of floss. The other end 861 of the piece of floss extends down along the flossing handle 815 to where it is anchored on another transversely oriented cleat 875.

In this form of the apparatus 810, the flosser is able to quickly adjust the length of the floss segment 836 while flossing. As new floss segments 836 are needed the flosser can quickly unwrap floss from the cleat 872, pull it through respective apertures from its free end 861, wrap the end 861 further around the cleat 875, and continue flossing without any delay.

The apparatus 810 also lends itself to further modification which results in a dual purpose apparatus; one which can also serve as a toothbrush. Such an apparatus is seen at 810A in FIG. 16.

FIG. 16 shows the apparatus 810A substantially identical to the apparatus 810 except that one handle can also function as a toothbrush. One gripping handle 816A has, on the end opposite its working floss segment end, a set 880A of bristles implanted to form a conventional brush, so that it can thus be used as a toothbrush.

Referring now to FIG. 17, still another modification of the second form of floss apparatus is illustrated at 1410. The apparatus 1410 is, in many respects, identical to the flossing apparatuses 710 and 810 hereinbefore discussed. As such, only portions of it are shown.

In the apparatus 1410, a virtual loop 1417 has free ends 1461 and 1462. The ends are threaded through apertures (not shown) in the handles 1415 and 1416. The free end 1462 is then wrapped numerous times around a rotatable spindle (not shown) within a storage drum 1480 fixed to the handle 1416.

The storage drum 1480 has a spindle latching button 1481 extending from it. The button 1481 is spring loaded outwardly into latching engagement with the spindle, thus normally preventing the spindle from rotating and allowing floss to be withdrawn. When the button 1481 is pressed, floss can be pulled from the drum.

Floss is drawn from the drum 1480 by pulling on the other end 1461 of the loop 1417. The floss is pulled through a brake block 1485 which has a one-way brake 1486 of conventional construction in it. The brake 1486 permits floss to pass through the brake block 1485 in one direction (down in FIG. 17), but prevents it from moving back through the block.

As will be seen, replacement floss in the loop 1417 can readily be made available for flossing by depressing the button 1481 and pulling the floss end 1461 through the brake block 1485. The end 1461 is then cut off on a conventional cutting element 1486 fastened to the handle 1415.

Referring now to FIG. 18, a third form of flossing apparatus embodying features of the invention is illustrated at 1510. The apparatus 1510 is designed to be operated with one hand H.

As illustrated, the apparatus includes a hollow handle 1515 which has a thumb shaped housing 1580, at one end, into which the user's thumb T is inserted. Another hollow handle 1516 has a middle finger-tip shaped housing 1581, at a corresponding end, into which the user's middle finger tip F is inserted.

A loop 1517 of floss interconnects the handles 1515 and 1516. The loop passes through apertures 1520 and 1521 in the handle 1515, and also through apertures 1530 and 1531 in the handle 1516. In doing so it passes through the hollow handles, as will be seen.

The loop 1517 is actually a length of floss which is threaded through the handles in the aforedescribed manner and, then, tied together by a knot 1535 at its opposite free ends. In this arrangement the loop 1517 formed has a working segment 1536 of floss between the free ends of the handles 1515 and 1516 and a control segment 1537 between its thumb and finger-tip housings 1580 and 1581.

Manipulation of the working floss segment 1536 is accomplished by manipulating the handles with the thumb and middle finger. At the same time the control segment 1537 is manipulated by the free index finger. The flossing operation advantages achieved with the previously described embodiments are also achieved with this one-handed embodiment.

Referring now to FIGS. 19 and 20, a laparoscopic surgery apparatus embodying features of one form another aspect of the invention is seen generally at 910. The apparatus 910 includes a conventional 12 mm O.D. laparoscope 911 containing an 8 mm I.D. channel 912 through which an operating assembly 913 extends.

The operating assembly 913 includes two hollow rods, 915 and 916, i.e., rods with corresponding passages 920 and 921 extending through them, from end to end. A flexible wire 925 extends through each of said passages and has its free ends tied together at 935 to form a loop 937.

The loop 937 includes a working segment 938 between adjacent one ends of the passages 920 and 921 and a control segment 939 between the opposite ends. With the operating assembly 913 in place in the laparoscope 911, and the scope inserted into a patient and properly positioned for surgery, the working segment 938 can be manipulated in 3-dimensions by manipulating the rods 915 and 916 from outside the patient's body while also manipulating the control segment 939 of the loop 937.

The working segment 938 can, accordingly, be used to position a device (e.g., a chemical or radioactive bead) or act as a ligature or, even carry an electrical current to a selected location. A ligature can be formed by wrapping the working segment 938 around an object inside the patient's body cavity. Used as an electrical current conductor the working segment can be used in electrodissection, figuration, etc., without the danger of grounding through unanticipated contact with an internal organ.

In use, the loop 937 of the operating assembly is manipulated like the flossing devices hereinbefore described, albeit on a more restricted basis. The constraint of the laparoscope channel I.D. is felt in manipulating the working segment 938, of course. Nevertheless, most of the advantages of positioning and control of the working segment 938 which are achieved are identical to those hereinbefore ascribed to the flossing apparatuses.

Another form of laparoscopic surgery apparatus embodying features of the invention is seen in FIG. 21 at 1210. The apparatus includes a conventional laparoscope 1211 through which an operating assembly 1213 extends.

The operating assembly 1213 is very similar in design to the flossing apparatus 1510 shown in FIG. 18. Two hollow rods 1215 and 1216 have passages extending through them. The rod 1215 has an open free end 1220 and an aperture 1221 adjacent its thumb held end. The rod 2516 has an open free end 1230 and an aperture 1231 adjacent its middle finger-tip held end.

A flexible wire 1225 extends through the handle passages to form a loop having a working segment 1238 and a control segment 1239. With the operating assembly 1213 in place in the laparoscope 1211, and the scope inserted with one hand into a patient and properly positioned for surgery, the working segment 1238 can be manipulated in three-dimensions with two fingers and the thumb on one hand.

Referring now to FIGS. 22 and 23, a laparoscopic surgery apparatus embodying features of another embodiment of the invention is seen generally at 1010. The apparatus 1010 includes two identical sleeves 1011 and 1012 of convention steel construction. The stainless sleeves have corresponding channels 1015 and 1016 extending through them and puncture points 1020 and 1021 formed at one end.

A flexible wire 1025 having hooked free ends 1026 and 1027 is threaded through the channels 1015 and 1016 into the patient's body cavity after the sleeves 1011 and 1012 have been inserted by puncture in the manner shown in FIG. 19. The free ends 1026 and 1027 of the wire 1025 are then connected by hooking them in the manner illustrated or by some other suitable technique; for example by magnetic coupling. A loop 1037 is thus formed extending into and out of the patient through the sleeves 1011 and 1012.

The loop 1037, like those previously discussed in other contexts, now has a working segment 1038 between adjacent puncture points 1020 and 1021 within the body cavity and a control segment 1039 between opposite ends outside the patient's body. The working segment 1038 can be manipulated in 3-dimensions by manipulating the sleeves 1011 and 1012 from outside the patient's body while also manipulating the control segment 1039 of the loop 1037. In use, the apparatus 1010 is manipulated in a manner apparent from descriptions of previous embodiments.

Now referring to FIG. 24, the invention is shown in yet another embodiment, an apparatus 1110 for mechanical cutting or abrasion. The apparatus 1110 comprises a pair of handles 1115 and 1116 interconnected by a loop or band 1117 of wire.

The handles 1115 and 1116 may be formed of stainless steel, for example. Each is about six inches long. Small apertures 1120 and 1121 are formed transversely through opposite ends of the handle 1115. Identical apertures 1130 and 1131 are formed through corresponding opposite ends of the handle 1116.

A length of high strength, alloy wire is threaded through the apertures 1120, 1130, 1131 and 1121, in that order. The free ends of the wire are then connected to a conventional, battery operated drive capstan 1132 fastened to the handle 1115.

A working segment 1138 of wire is then disposed between the aperture 1120 and 1130. The capstan 1132 can be operated to reciprocate that segment 1138 or to move it continuously in one direction (with a sufficient length of wire, or an endless wire). The working segment 1138 can be manipulated in space, in a manner hereinbefore made clear, to polish or cut a work piece; a jewel, for example.

On a larger scale the apparatus 1110 can function as a saw, i.e., in a "chain saw" operation. For example, the band 1117 of wire can be separable in its working segment 1138 and reconnected around a log. The mode of operation will be apparent from the foregoing description of other embodiments of the invention.

Referring now to FIG. 25, another form of apparatus for cutting or abrading is illustrated at 1310. The apparatus 1310 may be compared in structure and function to the apparatus 1110 seen in FIG. 24, except that its wire loop 1317 is a virtual loop rather than a real loop.

More specifically, the apparatus 1310 includes handles 1315 and 1316 having apertures 1320, 1321 and 1330, 1331 in them, respectively. A length of cutting or abrading wire is threaded through these apertures, as illustrated, and its opposite ends 1361 and 1362 are fastened to corresponding cleats 1371 and 1372 on the handles 1316 and 1315, respectively. In this regard the loop 1317 configuration is similar to that shown in FIG. 9.

The loop 1317 includes a working portion 1336 between the apertures 1320 and 1330 and segments 1338 and 1339 which extend along the sides of respective handles. These side segments 1338 and 1339 are routed over control rollers 1381 and 1832, the rollers being mounted on corresponding free ends of control members 1383 and 1384, respectively. The opposite end of each control member is pivotally connected to the end of a corresponding handle 1315 and 1316, as at 1391 and 1392.

Disposed between the handle 1315 and the control member 1384 is a coil spring 1395 of conventional construction. The coil spring 1395 is under compression and, as such, tends to urge the roller 1382 away from the handle 1315 and the roller 1381 towards the handle 1316.

In use in an abrading operation, for example, the operator grips the handles 1315 and 1316 near the pivots 1391 and 1392 of the control members. The working segment 1336 of the loop is ideally positioned on a work surface by arranging the handles 1315 and 1316 in space, constrained only by the loop 1317. The control member 1383 is then rhythmically pivoted away from and toward control member 1384 follows as the spring 1395 compresses and expands. The working segment 1336 moves back and forth through the apertures 1320 and 1330 and abrades the work piece as it does so.

Figure 27:
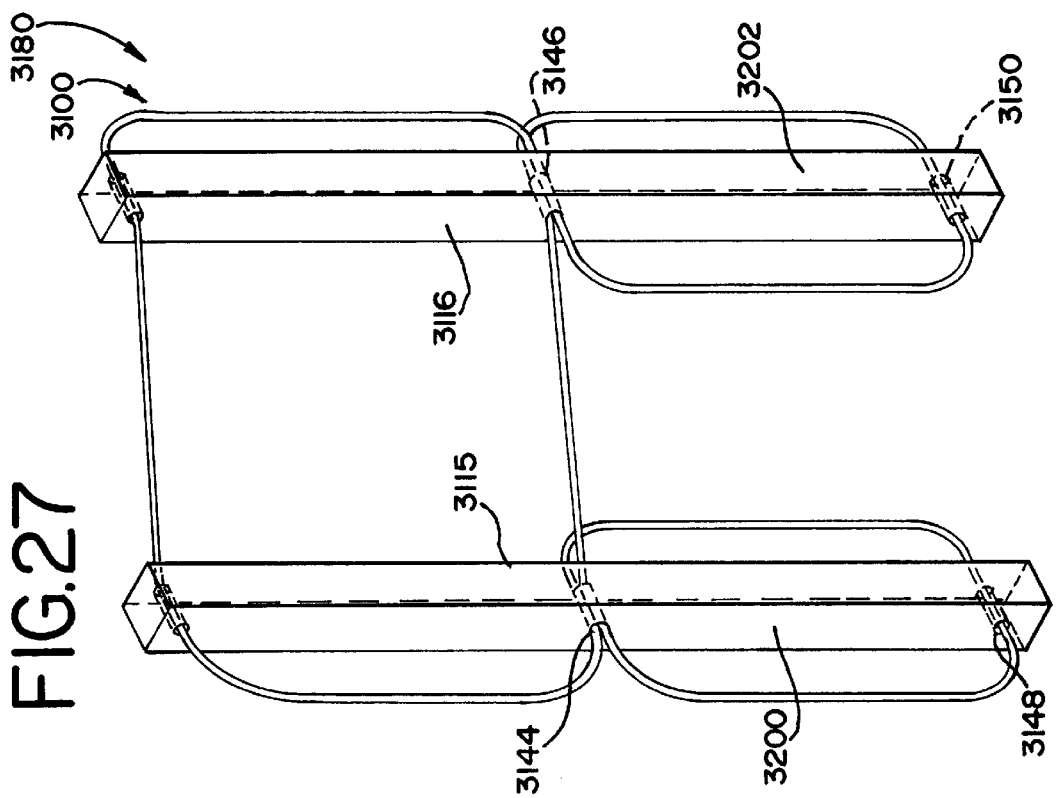
FIG. 27 is a perspective view of a variation of the flossing apparatus of FIG. 26 incorporating the present invention.
Figure 26:
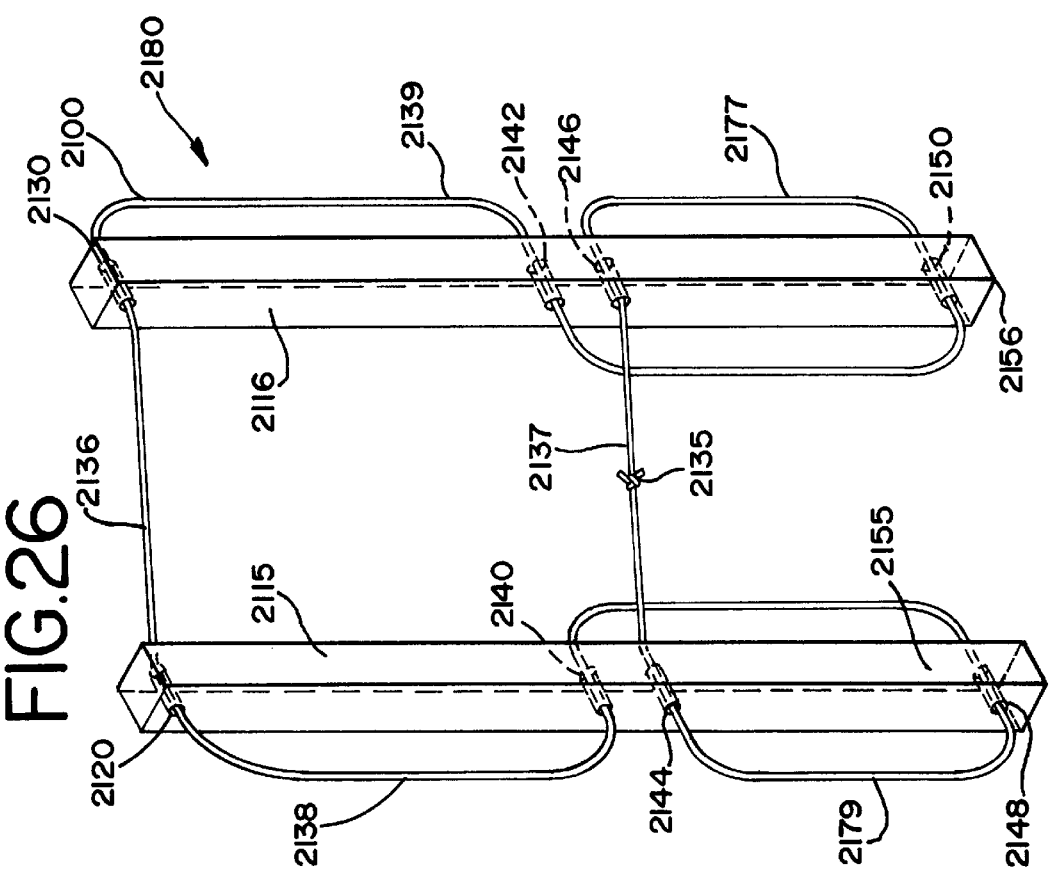
FIG. 26 is a perspective view illustrating another form of the flossing apparatus embodying features of a variation of the present invention.

FIGS. 26 through 28 illustrate yet other embodiments of the invention. A flossing apparatus 2180 is shown in FIG. 26 which is similar, in some respects, to that shown in FIG. 7 at 180. The flossing apparatus 3180 shown in FIG. 27 and the flossing apparatus 4180 shown in FIG. 28 are, in turn, variations of the apparatus 2180 shown in FIG. 26.

As shown in FIG. 26, each of the elongated handles 2115 and 2116 of the flossing apparatus 2180 have four transverse apertures therethrough. Upper apertures 2120 and 2130 are located in corresponding upper portions of the handles 2115 and 2116, respectively, while lower apertures 2148 and 2150 are located in corresponding lower portions. Pairs of middle apertures 2140, 2144 and 2142, 2146 are located between the upper and lower apertures in corresponding handles 2115 and 2116.

A continuous loop comprised of a flexible element 2100 is threaded through the apertures, as shown. Preferably, commonly available dental floss is used, although other flexible elements may be utilized while remaining within the scope of the present invention. The flexible element 2100 is threaded in a fashion similar to that described in the previous embodiments, with a length of the element extending between the upper apertures 2120 and 2130, and defining a working segment 2136. Upper side segments 2138 and 2139 of the flexible element 2100 are disposed along the upper portions of the handles 2115 and 2116, respectively.

The side segments 2138 and 2139 terminate at lower ends by threading through corresponding ones of the middle apertures 2140 and 2140. The remaining portion of the loop 2100 then travels down alongside the lower portions 2155 and 2156 of corresponding handles and through corresponding lower apertures 2148 and 2150, before traveling up alongside corresponding lower portions 2155 and 2156 and inwardly through the lower middle apertures 2144 and 2146. The loop 2100 is then closed with a knot at 2135 to form a control segment 2137 extending between the middle apertures 2144 and 2146 on the handles.

In the aforedescribed configuration, the lower apertures 2148 and 2150, in combination with one of the middle apertures 2144, 2140 and 2146, 2142, create an integral spooling structure on the lower portions 2155 and 2156 of each of the handles 2115 and 2116. While other spooling structures have previously been disclosed, the present embodiment is advantageous because the structure is so simple and requires only the handle portions themselves. With a portion of the floss threaded through the spooling structure, a bollard-like frictional retention force is maintained on the floss element 2100 to allow the user to more easily retain the floss in position within the apertures. The frictional retention force may be enhanced by utilizing pressure from the fingers on the side portions of the floss at 2177 and 2179, or by increasing tension in the floss by pulling the handles 2115 and 2116 further apart.

Use of the spooling structure described permits the apparatus 2180 to hold a relatively large loop of floss without the need for complicated winding structures. As a result, the apparatus 2180 can be prepackaged with an installed loop of floss 2100 of sufficient length to adequately floss all the teeth in the mouth using a fresh, unused portion of the working segment 2136 for each tooth space. The user may tension the floss 2100 by pulling the handles apart and/or tensioning one of the side segments of floss, such as 2138 or 2139. As the user finishes flossing each space, the floss may be advanced as previously described to introduce a fresh working segment. For example, the user may relieve tension on the floss and advance the floss through the apertures by alternately pressing one of the side segments 2139, 2177, 2138 or 2179 against the handles 2115 and 2116 and manipulating the handles as previously described. When the user is finished flossing the entire mouth, a minimum of unused floss is left over and the entire apparatus 2180 may be discarded.

During use, manipulation of the side segments in the apparatus 2180 allows for control of the tension in the floss or advancing it through the apertures in the same fashion as with the embodiment illustrated in FIGS. 5–7. Furthermore, additional side control segments 2179 and 2177 are formed on both the inside and the outside edges of the lower portions 2155 and 2156 of the handles. This allows more complete control of the tension in the flexible element 2100 and the looseness of the element 2100 within the apertures.

It should also be understood that the spooling means need not hold only one winding of flexible element on each handle. Several windings may be made between the middle and lower apertures to increase the total amount of floss stored on the apparatus 2180.

Referring now to FIG. 27, a variation of the flossing apparatus 2180 is shown at 3180. The apparatus 3180 is similar to the apparatus 2180 of FIG. 26, but instead of a pair of middle apertures on each handle 3115 and 3116, only single middle apertures 3144 and 3146 are formed in corresponding handles 3115 and 3116. Preferably, the middle apertures 3144 and 3146 are slightly larger than the other apertures in the apparatus to allow several pieces of the floss 3100 to pass loosely therethrough.

Modifications to the middle apertures 3144 and 3146 and the lower apertures 3148 and 3150 may also be made to refine the operation of the apparatus 3180. For example, as shown in FIG. 27A, the cross-sectional profiles of the middle apertures 3144A and 3146A may be slightly curved toward the lower end of the handles 3200A and 3202A, and the profiles of the lower apertures 3148A and 3150A may be slightly curved toward the upper end of the handles. The curvatures in these apertures permits improved sliding of the flexible floss 3100 within the apertures by decreasing sliding friction.

As shown in FIG. 27B, in another modification the middle apertures 3146B (only one shown) may also be fluted in cross-section as at area 3147B. This fluted configuration decreases the sliding friction of the floss 3100 extending both above and below the apertures on the handle 3202A. The fluted profiles are preferably used when multiple wrappings of flexible element are desired on the spooling structure.

With the apparatus 3180, as with the apparatus 2180 previously discussed, an amount of floss can be stored between the middle and lower apertures on each handle 3115 or 3116. The floss is freely slidable within each of the apertures to allow advancement of the loop 3100 through the apertures and around the spooling apparatuses 3200 and 3202.

Referring now to FIG. 28, another variation of the flossing apparatus is shown at 4180. The apparatus 4180 includes a pair of spooling structures 4200 and 4202 mounted on the outside portions of the handles 4115 and 4116, respectively. The spooling structures 4200 and 4202 are race-track shaped and fixed to respective handles around which looped portions 4100A and 4100B of the floss 4100 are wound. The windings are made around the periphery of the structures 4200 and 4202. Each periphery has a curved cross-section trough shape to allow the floss 4100 to slide easily off the structures when sufficiently unterisioned as described above.

The spooling structures 4200 and 4202 shown in FIG. 28 allow for more floss in the continuous loop 4100 to be stored externally of the handles 4115 and 4116. The top portions of the structures 4200 and 4202 also provide a convenient thumb-placement grip for the handles 4115 and 4116 during use. A cap member 4400 is also preferably mounted to the outer portion of each spooling structures 4200 and 4202, and projects an annular lip 4420 radially away from the transverse axis of the spooling means. The lip 4420 prevents undesired unwinding of the floss portions 4100A and 4100B from around the spooling means.

One skilled in the art would recognize that various modifications can be made to the configurations described herein. For example, the spooling means can include structures such as hooks, bollards, transversely projecting cleats or other structures. Also, the spooling means need not require winding of the floss around generally transverse structures as shown. Floss may be wound around the handles themselves and routed through a variety of apertures to present a usable working segment, operating segment or both.

Furthermore, it should be noted that the handles of the embodiments described above do not both need to include the spooling means structures described. Only one such structure on one of the two handles is necessary to achieve the result described. In the alternative, more than one such structure may be defined on or mounted on each handle to retain a greater amount of spare floss. Note also that, preferably, as in the case of most of the previously discussed preferred embodiments, any cross-sectional shape of the flossing handles may be utilized, whether the handles have cross-sectional areas that are flat, round, hollow or curved.

These devices may also be utilized in modified form to accomplished similar objectives as the other embodiments disclosed in the present specification. For example, similar structures and devices may be configured to perform laparascopic surgery or for cutting or abrading as previously described.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

We claim:

1. An apparatus for moving a flexible element, said apparatus comprising:
    a) first and second elongated handles, each of said handles having at least an upper and a lower aperture formed therein;
    b) at least one central aperture formed in each of said first and second handles, said central aperture being positioned between said upper and lower apertures; and
    c) a flexible element extending through and freely slidable within each of said apertures in each of said handles;
    d) wherein manipulation of said handles in conjunction with pressure applied to said loop of flexible element advances said element through said apertures to change the position of said flexible element relative to said handles.

2. The apparatus of claim 1 further comprising a spool for the flexible element on at least one of said handles between a central aperture and a lower aperture, a portion of said flexible element being slidably wound around said spool.

3. The apparatus of claim 2 wherein said spool is formed integrally with each of said first and second elongated handles.

4. The apparatus of claim 3 wherein said at least one central aperture and said lower aperture are curved around said spool to facilitate the sliding of said flexible element around said spool.

5. The apparatus of claim 2 wherein said spool is mounted externally to each of said handles.

6. An apparatus for moving a flexible element, said apparatus comprising:
    a) first and second elongated handles, each of said handles having at least an upper aperture, a lower aperture, and a middle aperture defined therethrough; and
    b) a loop of flexible element extending between said handles through said upper apertures, said element wound between said lower and middle apertures and extending between said handles through at least said middle or lower apertures;
    c) wherein the portion of said element extending between said upper apertures defines a working segment, and the manipulation of said handles in conjunction with pressure applied to said loop of flexible element advances said element through said apertures to change the portion of flexible element comprising said working segment.

7. The apparatus of claim 6 wherein said middle apertures means further comprises a pair of transversely extending apertures defined within said elongated handles between said upper and lower apertures.

8. The apparatus of claim 7 wherein said pair of apertures extend substantially parallel to each other.

9. The apparatus of claim 7 wherein at least one of said pair of middle apertures means and said lower apertures are curved to define a spool on each of said handles, said spool for retaining a wrapped portion of said flexible element.

10. The apparatus of claim 6 wherein said middle aperture further comprises a single aperture defined within said elongated handles between said upper and lower apertures.

11. The apparatus of claim 10 wherein said middle aperture is wider than said upper and lower apertures.

12. The apparatus of claim 6 further comprising a spooling means defined on at least one of said handles between said middle aperture means and said lower apertures, a portion of said flexible element being wrapped around said spooling means and slidably retained thereon.

13. The apparatus of claim 12 wherein said flexible element is wrapped between a portion of said middle apertures and said lower apertures on at least one of said handles.

14. The apparatus of claim 13 wherein said flexible element is freely slidable within a portion of said middle apertures and said lower apertures.

15. An apparatus for moving a flexible element, said apparatus comprising:
   a) first and second elongated handles, each of said handles having at least one aperture defined through an upper portion of said handles and a pair of lower apertures defined through a lower portion of said handles;
   b) a loop of flexible element extending through each of said apertures; and
   c) spooling means defined between said lower apertures on each of said lower portions for slidably retaining a portion of said loop of flexible element.

16. The apparatus of claim 15 wherein said spooling means further comprises a portion of said handles extending between said lower apertures and a middle aperture defined in said handle between said upper and lower handles, a portion of said flexible element being slidably wrapped between said upper and lower apertures.

17. The apparatus of claim 15 wherein said spooling means further comprises a member mounted to said handle for receiving a portion of said flexible element wound around said member, said flexible element slidable around said member.

18. The apparatus of claim 17 wherein said spooling means further includes a thumb rest portion.

19. The apparatus of claim 18 further comprising a retention member mounted over said spooling portion to prevent unwinding of said flexible element from said member.

20. An apparatus comprising:
   (a) first and second elongated handles, said handles having a set of apertures defined through portions of said handles, including at least one aperture defined through an upper portion of said handles, a pair of lower apertures defined through a lower portion of said handles, and a third pair of apertures defined through a middle portion of said handles between said upper and lower portions of said handles; and
   (b) a flexible element, a first portion of said element extending between said handles through the aperture defined through the upper portion of said handles, a second portion of said element disposed between the upper portion of said handles and the middle portion of said handles; a third portion of said element extending between the third pair of apertures; and the remainder of said element disposed between the third pair of aperture and the lower apertures of said handles.

21. An apparatus comprising:
   (a) a first elongated handle;
   (b) a second elongated handle;
   (c) a set of apertures comprising an upper apertures disposed in an upper portion of each of said first and second handles, a lower aperture disposed in a lower portion of each of said first and second handles, and a middle aperture disposed in each of said first and second handles between said upper and lower apertures; and
   (d) a flexible element, a first portion of said element extending between said handles through said upper apertures, a second portion of said element disposed along said handle between said upper and middle apertures, a third portion of said element extending between said handles through said middle apertures, and the remainder of said element disposed along said handles between said middle and lower apertures.

22. An apparatus for moving a flexible element, said apparatus comprising:
   a) first and second elongated handles, each of said handles having an upper aperture and a lower aperture;
   b) each of said handles also having a central aperture therein positioned between corresponding upper and lower apertures;
   c) a flexible element extending through each of said apertures in each of said handles so as to form an upper virtual loop between said first and second handles above said central apertures and a lower virtual loop between said first and second handles below said central apertures, the portion of said upper virtual loop between said upper apertures comprising a working portion of the flexible element, said flexible element having opposite free ends which are connected;
   d) wherein said flexible element can be advanced through said apertures to change the position of said working portion relative to said handles by manipulating said handles while applying pressure to said flexible element in said lower virtual loop.

* * * * *